United States Patent [19]

Wakatsuki et al.

[11] Patent Number: 4,845,239

[45] Date of Patent: Jul. 4, 1989

[54] PHOSPHORIC ESTERS AND PROCESS FOR PREPARING THE SAME

[75] Inventors: Junya Wakatsuki; Tohru Katoh; Akira Matsunaga, all of Wakayama; Tomihiro Kurosaki, Osaka, all of Japan

[73] Assignee: Kao Corporation, Tokyo, Japan

[21] Appl. No.: 32,627

[22] Filed: Apr. 1, 1987

[30] Foreign Application Priority Data

Apr. 21, 1986 [JP] Japan .................................. 61-91704

[51] Int. Cl.⁴ .............................................. C07F 9/09
[52] U.S. Cl. .................................................. 549/219
[58] Field of Search ....................... 549/219, 218, 216

[56] References Cited

FOREIGN PATENT DOCUMENTS 1109405  8/1984  U.S.S.R. .............................. 549/219

OTHER PUBLICATIONS

Soviet Inventions Illustrated, Section Ch: Chemical, week 8511, Apr. 24, 1985; Class G, p. 5, No. 85-067496/11, Derwent Publications LTD, London, GB; & SU-A-1 109 405 (Lengd Cine-Eng. Inst.) 8-2-3-1984.

Wende et al., "Epoxy Esters of Some Phosphorous Acids", CA 64, 5026h–5027a, 1966.

E. Mularczyk et al, Tenside Detergents, vol. 21, (1984), "Glycidyl Esters of Dialkylphosphoric Acids", pp. 194–196.

Primary Examiner—Glennon H. Hollrah
Assistant Examiner—Susan P. Treanor
Attorney, Agent, or Firm—Oblon, Spivak, McClelland, Maier & Neustadt

[57] ABSTRACT

A novel phosphoric ester of the following formula (I)

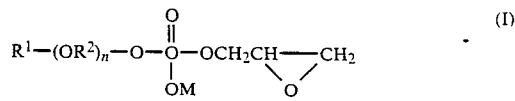

is prepared by reacting a phosphoric ester of the following formula (II)

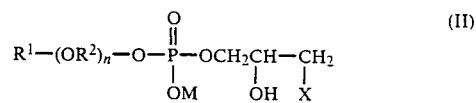

with a basic compound.

By reacting the phosphoric ester (I) with various types of amine compounds or other acidic hydrogen-bearing compounds, various phospholipid analogue compounds or phosphoric esters can be derived.

2 Claims, 2 Drawing Sheets

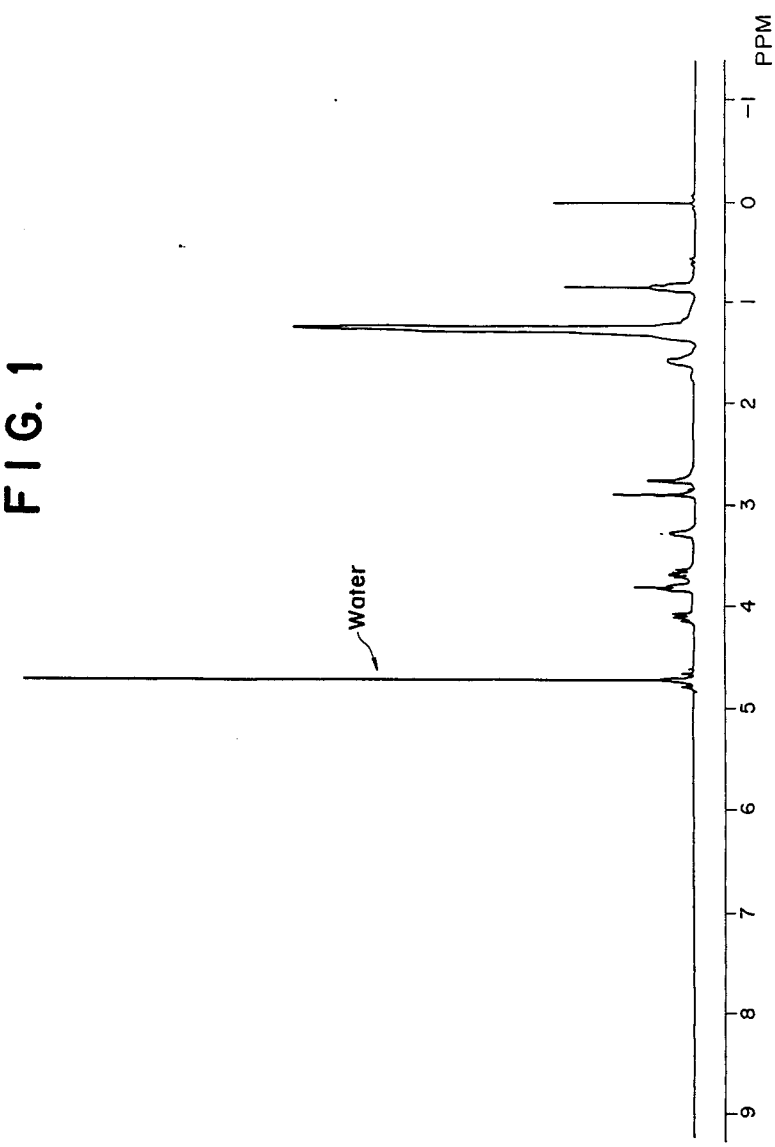

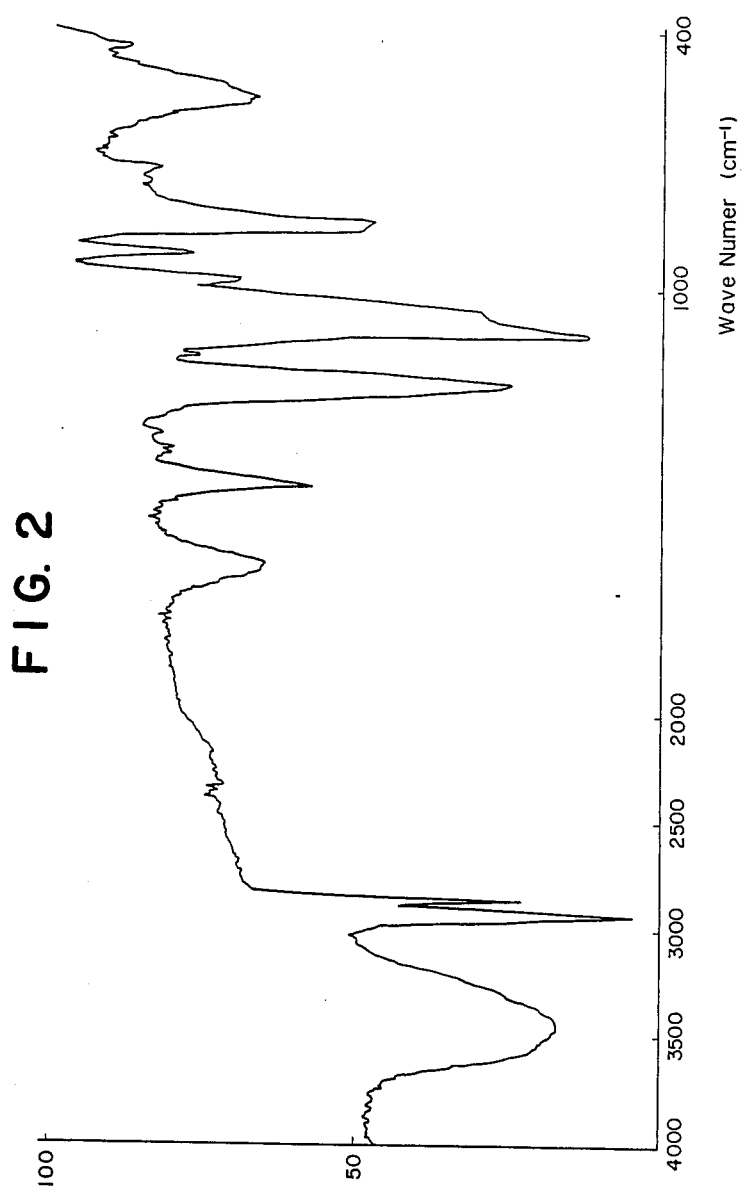

PHOSPHORIC ESTERS AND PROCESS FOR PREPARING THE SAME

BACKGROUND OF THE INVENTION (1) Field of the Invention

This invention relates to novel phosphoric esters and more particularly, to phosphoric esters of the following general formula (I)

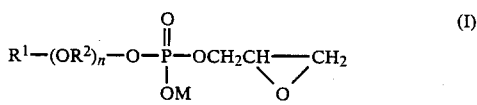

in which $R^1$ represents a linear or branched alkyl or alkenyl group having from 1 to 36 carbon atoms, in which hydrogen atoms are optionally replaced by fluorine atoms, or a phenyl group substituted with a linear or branched alkyl group having from 1 to 15 carbon atoms, $R^2$ represents an alkylene group having 2 or 3 carbon atoms, n is a value of from 0 to 30, and M represents a hydrogen atom, an alkali metal, an alkaline earth metal, ammonium, an alkylamine or an alkanol amine. The invention also relates to a process for preparing the phosphoric esters.

(2) Description of the Prior Art

Phospholipids are amphiphilic compounds having both a hydrophobic moiety and a hydrophilic moiety in the molecule thereof and are utilized, as biosurfactants, in wide fields of cosmetics, foods and medicines by making use of their emulsifying, dispersing, foaming and moisture-retaining functions. The phospholipids in vivo are constituent components of cell membranes and have various functions of cell partition and sectional formation, and transport of substances. In recent years, it has been clarified that they play an important role in various biological activities.

The phospholipids have, in most cases, such a phosphoric diester structure that the hydrophobic and hydrophilic moieties are joined through a phosphoric ester bond. Moreover, the hydrophilic moiety has a complicated structure such as a betaine structure having a phosphoric acid group and an amino group or an amino acid group, or a structure having a phosphoric acid group, a charge-free glycerine group and a sugar group. The properties of a phospholipid depend on the structure of the hydrophilic moiety.

Accordingly, if phospholipids or analogues thereof could be chemically prepared, they would be applicable not only to cosmetics and medicines, but also to a wide variety of other general industrial products. A number of attempts have been made to chemically prepare phosphlipids or analogous compounds thereof. Most of them require multi-step reactions, so that intended products can be obtained only in low yield and thus, the industrial production was not successful [e.g. Bear et al, J. Amer. Chem. Soc., 72, 942, (1950)]. Accordingly, there is a demand for the preparation of phospholipid analogue compounds in an industrial and simple manner. Moreover, if precursors which permit easy introduction of, for example, an amino group and an amino acid group other than a phosphoric acid group of the hydrophilic moiety could be industrially prepared, preparation of various types of phospholipid analogue compound would become possible.

On the other hand, many studies have been made in the field of polymers in order to impart the properties of a phosphorous moiety to polymer compounds. More particularly, polymerization of polymerizable group-bearing phosphorus-containing compounds as monomers and modification of polymeric compounds with phosphorus-containing compound have been extensively studied.

It has been made clear that a cell membrane has a bimolecular phospholipid membrane (which is oriented in a good order owing to physical properties of phospholipid molecules, or a self-organizing tendency inherent to an amphiphilic compound having both hydrophobic and hydrophilic groups in which the molecules gather and set up by themselves). Studies have been made to artificially prepare the bilayer film vesicle (liposome) and apply it as a model of a biomembrane or as a microcapsule. Further, the bimolecular membrane structure is converted into a macromolecule, i.e. a phospholipid analogue compound having a polymerizable hydrophobic or hydrophilic group is prepared. For instance, Regen et al prepared a compound of the following formula (III) [J. Amer. Chem. Soc., 105, 2975 (1983)].

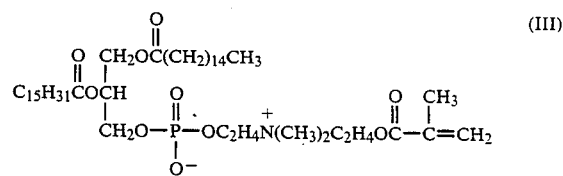

However, the preparation of these substances requires multi-step reaction steps, making the industrial production difficult.

The glycidyl group is a functional group which is not only polymerizable, but also highly reactive with various groups such as, for example, an amino group, a carboxyl group and the like, to give adducts. If the glycidyl group can be introduced into the phosphoric acid group, the resultant product serves not only as a phosphorus compound for monomer, but also as a modifying agent for polymers. Moreover, if the phosphorus compound having the glycidyl group has such an amphiphilic structure as phospholipids, i.e. if it has a glycidyl group aside from a structure having a hydrophobic group and a phosphoric acid group serving as a hydrophilic groups, it may be converted to a precursor which is important in preparing a phospholipid analogue compound as set forth before, or may be used as a polymerizable group-bearing phospholipid analogue compound or as a precursor thereof.

However, only a few phosphoric esters having a glycidyl group are known up to now, including compounds in which 2 moles of glycidyl groups are joined to a phosphoric monoester, e.g. compounds of the following formula (IV) prepared by Rizpolozhenskii et al [Izv. Akad. Nauk SSSR, Ser. Khim., (9), 2006(1967)]

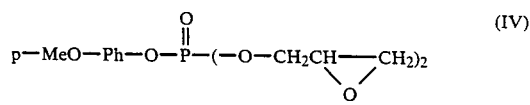

in which Ph represents a phenyl group; and compounds in which 1 mole of a glycidyl group is joined to a phosphoric diester, e.g. compounds of the following formula (V) prepared by Mularczyk et al [Tenside Detergents, 21, #4, 194(1984)]

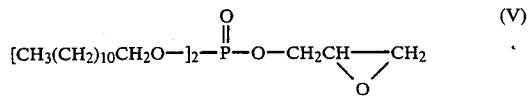

These compounds are free of a phosphoric acid group acting as a hydrophilic group. The above compounds, therefore, cannot be a precursor for phospholipid analogue compounds since they do not have all the moieties as described before, that is, a hydrophobic group, a phosphoric acid group as a hydrophilic group and a glycidyl group.

SUMMARY OF THE INVENTION

Under these circumstances, the present inventors made intensive studies and, as a result, found that when a phosphoric ester having a specific type of group is reacted with a basic compound, a compound having a hydrophobic group, a phosphoric acid group as a hydrophilic group, and a glycidyl group can be readily prepared and that the resulting phosphoric ester can act as a monomer and also is able to react with an active site of polymers, so that the phosphoric ester group can be introduced into the polymers. It was also found that the phosphoric ester can be a precursor which reacts with amine compounds, amino acids or sugars for conversion into various phospholipid analogue compounds. The present invention was accomplished based on the above findings.

Accordingly, the present invention provides novel phosphoric esters of the formula (I). Also, the invention provides a novel process for preparing phosphoric esters of the formula (I).

BRIEF DESCRIPTION OF THE DRAWINGS

FIG. 1 is a chart of an 1H NMR spectrum of sodium dodecyl glycidyl phosphate obtained in Example 1; and FIG. 2 is a chart of an infrared absorption spectrum of sodium dodecyl glycidyl phosphate obtained in Example 1.

DETAILED DESCRIPTION OF THE INVENTION AND PREFERRED EMBODIMENTS

In the phosphoric esters of the formula (I) according to the invention, $R^1$ represents a linear or branched alkyl or alkenyl group, whose hydrogen atoms may be replaced with fluorine atoms and which have from 1 to 36 carbon atoms, or a phenyl group substituted with a branched alkyl group having from 1 to 15 carbon atoms. Examples of the alkyl or alkenyl group, or the phenyl group include methyl, ethyl, butyl, octyl, decyl, dodecyl, tetraecyl, hexadecyl, octadecyl, docosyl, tetracosyl, triacontyl, 2-ethylhexyl, 2-octyldodecyl, 2-dodecylhexadecyl, 2-tetradecyloctadecyl, monomethylbranched isostearyl, tridecafluorooctyl, heptadecafluorododecyl, heneicosafluorododecyl, pentacosafluorotetradecyl, nonacosafluorohexadecyl, tritriacontafluorooctadecyl, 2-pentafluoroethylpentanfluorohexyl, 2-tridecafluorohexyltridecafluorodecyl, 2-heptadecafluorooctylheptadecafluorododecyl, 2-heneicosafluorodecylheneicosafluorotetradecyl, 2-pentacosafluorododecylpentacosafluorohexadecyl, 2-nonacosafluorotetradecylnonacosafluorooctadecyl, octenyl, decenyl, dodecenyl, tetradecenyl, hexadecenyl, octadecenyl, dococenyl, tetracocenyl, triacontenyl, nonylphenyl, and the like. Of these, those groups having from 8 to 36 carbon atoms are preferred in view of the surface activity and self-organizability.

The phosphoric esters (I) of the invention can be prepared according to the novel process indicated, for example, by the following reaction formula

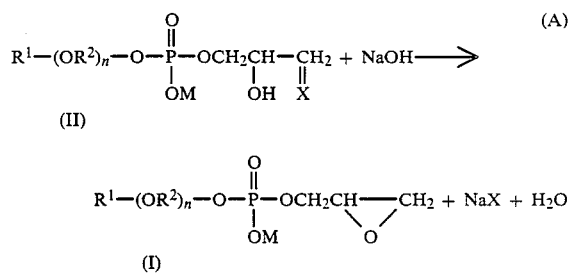

in which $R^1$, $R^2$, M and X have the same meanings defined before provided that when M=hydrogen atom, one more equivalent of NaOH is necessary in the reaction formula (A).

The phosphoric ester of the general formula (II) as indicated in the above formula (A) may be those obtained by any processes or methods. For instance, a monoalkali metal salt of a highly pure phosphoric monoester having suitable $R^1$ and $R^2$ groups is reacted with an epihalohydrin to obtain the ester.

Moreover, the phosphoric ester can be obtained by reacting 1 mole of an organic hydroxy compound having suitable $R^1$ and $R^2$ groups and 1 mole of 3-halo-1,2-propanediol with 1 mole of phosphorus oxychloride, followed by hydrolysis.

The solvents used for the reaction are preferably polar solvents and include, for example, water, methyl alcohol, ethyl alcohol and the like.

The reaction temperature is in the range of from $-30°$ C. to $100°$ C. In order to prevent further reactions of the resultant product with water or an alcohol as a solvent, lower temperatures are preferred. In this sense, the reaction at $-10°$ to $50°$ C. is preferred.

The basic compound may be, aside from sodium hydroxide as indicated in the reaction formula (A), alkali metal hydroxides such as potassium hydroxide, alkaline earth metal hydroxides such as calcium hydroxide, and organic amine compounds. Of these, sodium hydroxide and potassium hydroxide are preferred. The amount may be equimolar to or higher than the amount of the compound of the formula (II). In general, an equimolar amount or a slight excess is used. The reaction proceeds quantitatively according to the reaction formula (A). It will be noted that when M=hydrogen atom in the compound of the formula (II) in the reaction formula (A), one more equivalent of the basic compound is necessary.

In the reaction formula (A), although the salt is secondarily produced, the reaction product may be used, as it is, as the compound of the invention, which may depend on the purpose. In order to remove the salt, however, the reaction is conducted in ethanol to allow the salt to be precipitated, followed by separation by filtration.

When the phosphoric ester (I) of the invention is reacted, for example, with an amine compound according to the following reaction formula (B), a phospholipid having a quaternary ammonium group in the molecule as will be difficult to obtain industrially in prior art, i.e. an amphiphilic compound of the betaine structure having a phosphoric acid group and ammonium group as the hydrophilic moiety, can be readily obtained. Similarly, the reaction with other various types of amine compounds and other acidic hydrogen-bearing compound can derive various phospholipid analogue compounds and various phosphoric esters. The polymerizability of the glycidyl group itself or its reactivity with polymers ensures utility as a monomer, and a modifier for polymers and also for proteins.

In the reaction formula (B), when an amine compound to be reacted with phosphoric ester (I) of the invention is suitably selected to have a polymerizable group as $R^3$, $R^4$ or $R^5$, there can be readily obtained compounds having such a structure as a phospholipid analogue monomer having the similar betaine structure as indicated in the formula (III), i.e. compounds having hydrophobic moiety, a betaine structure serving as a hydrophilic moiety having the phosphoric acid group and the amino group, and a polymerizable moiety.

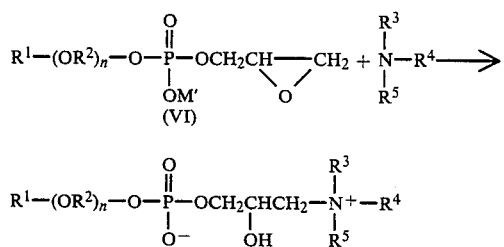

in which $R^1$ and $R^2$ have, respectively, the same meanings as defined before, $M'$ represents an alkali metal or an alkaline earth metal, and $R^3$, $R^4$ and $R^5$ are, respectively, a hydrogen atom or an organic group.

The present invention is described by way of examples.

EXAMPLE 1

50 g (0.13 mol) of sodium dodecyl 2-hydroxy-3chloropropyl phosphate was charged into a reactor, to which 1000 ml of ethanol was added, followed by agitation and heating to 70° C. to give a uniform system. Thereafter, the reaction system was cooled down to room temperature, to which 62.5 g (0.13 mol) of a 0.0021 mol/g sodium hydroxide solution in ethanol was gradually added and agitated for 3 hours while keeping the temperature. The high performance liquid chromatography (hereinafter referred to as HPLC) analysis revealed that the peak for the starting material disappeared and a peak for a new product appeared. The precipitated NaCl was removed by filtration, followed by distillation of the ethanol under reduced pressure to obtain 46 g of sodium dodecyl glycidyl phosphate (yield 100%). $^1$H NMR (D$_2$O, $\delta$(ppm)): see FIG. 1

0.8 (t, 3H, —P—OCH$_2$CH$_2$(CH$_2$)$_9$CH$_3$)
1.3 (broad s, 18H, —P—OCH$_2$CH$_2$(C̲H$_2$)$_9$CH$_3$)
1.6 (broad, 2H —P—OCH$_2$C̲H$_2$(CH$_2$)$_9$CH$_3$)

2.8, 2.9 (m, 2H, —P—OCH$_2$CH——C̲H$_2$)
\O/

3.3 (broad, 1H, —P—OCH$_2$C̲H——CH$_2$)
\O/

3.6–4.2 (m, 4H, C̲H$_2$——CHC̲H$_2$O—P—OC̲H$_2$)
\O/

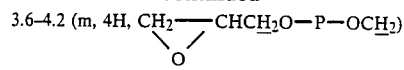

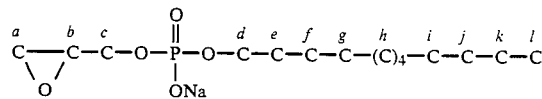

$\delta$(ppm) l; 14.1, k; 22.7, f; 26.1, g, i; 29.5, h; 29.7, e; 29.8, j; 32.0, a; 44.3, b; 50.9, d; 71.5, c; 77.

IR (KBr): see FIG. 2

| | Elementary analysis | | |
|---|---|---|---|
| | C (%) | H (%) | P (%) |
| Found | 51.30 | 8.62 | 8.8 |
| Calculated | 52.32 | 8.78 | 9.0 |

EXAMPLE 2

50 g (0.11 mol) of sodium 2-hexadecyl 2-hydroxy-3-chloropropylphosphate was charged into a reactor, to which 1000 ml of ethanol was added, followed by agitation and heating to 70° C. to obtain a uniform mixture. Thereafter, the reaction system was cooled down to 30° C., to which was gradually added 54.5 g (0.11 mol) of a 0.0021 mol/g sodium hydroxide ethanol solution, followed by agitation for 4 hours while keeping the temperature. The HPLC analysis revealed the disappearance of a peak of the starting material with a peak for the resultant new product appearing. The resultant NaCl precipitate was removed by filtration and the ethanol was distilled off under reduced pressure to obtain 45 g (yield: 98%) of sodium 2-hexyldecyl glycidyl phosphate.

| | Elementary analysis | | |
|---|---|---|---|
| | C (%) | H (%) | P (%) |
| Found | 55.90 | 9.39 | 7.8 |
| Calculated | 56.99 | 9.56 | 7.7 |

EXAMPLE 3

50 g (0.19 mol) of sodium butyl 2-hydroxy-3chloropropyl phosphate was charged into a reactor, to which 1000 ml of ethanol was added, followed by agitation and heating to 70° C. to obtain a uniform mixture. Thereafter, the reaction system was cooled down to room temperature, to which was gradually added 88.6 g (0.19 mol) of a 0.0021 mol/g sodium hydroxide ethanol solution, followed by agitation for 3 hours while keeping the temperature. The HPLC analysis revealed the disappearance of a peak of the starting material with a peak for the resultant new product appearing. The resultant NaCl precipitate was removed by filtration and the ethanol was distilled off under reduced pressure to obtain 43 g (yield: 100%) of sodium butyl glycidyl phosphate.

| | Elementary analysis | | |
|---|---|---|---|
| | C (%) | H (%) | P (%) |
| Found | 35.52 | 5.96 | 13.0 |

|  | Elementary analysis | | |
|---|---|---|---|
|  | C (%) | H (%) | P (%) |
| Calculated | 36.22 | 6.08 | 13.3 |

EXAMPLE 4

50 g (0.097 mol) of sodium trioxyethylenedodecyl ether 2-hydroxy-3-chloropropyl phosphate was charged into a reactor, to which 1000 ml of ethanol was added, followed by agitation and heating to 80° C. to obtain a uniform mixture. Thereafter, the reaction system was cooled down to 30° C., to which was gradually added 44.3 g (0.097 mol) of a 0.0022 mol/g sodium hydroxide ethanol solution, followed by agitation for 4 hours while keeping the temperature. The HPLC analysis revealed the disappearance of a peak of the starting material with a peak for the resultant new product appearing. The resultant NaCl precipitate was removed by filtration and the ethanol was distilled off under reduced pressure to obtain 46 g (yield: 99%) of sodium trioxyethylenedodecyl ether glycidyl phosphate.

|  | Elementary analysis | | |
|---|---|---|---|
|  | C (%) | H (%) | P (%) |
| Found | 51.87 | 8.71 | 6.4 |
| Calculated | 52.93 | 8.88 | 6.5 |

EXAMPLE 5

50 g (0.12 mol) of sodium nonylphenyl 2-hydroxy-3-chloropropyl phosphate was charged into a reactor, to which 1000 ml of ethanol was added, followed by agitation and heating to 80° C. to obtain a uniform mixture. Thereafter, the reaction system was cooled down to 30° C., to which was gradually added 53.0 g (0.12 mol) of a 0.0022 mol/g sodium hydroxide ethanol solution, followed by agitation for 4 hours while keeping the temperature. The HPLC analysis revealed the disappearance of a peak of the starting material with a peak for the resultant new product appearing. The resultant NaCl precipitate was removed by filtration and the ethanol was distilled off under reduced pressure to obtain 45 g (yield: 98%) of sodium nonylphenyl glycidyl phosphate.

|  | Elementary analysis | | |
|---|---|---|---|
|  | C (%) | H (%) | P (%) |
| Found | 54.11 | 7.58 | 7.8 |
| Calculated | 55.10 | 7.71 | 7.9 |

EXAMPLE 6

50 g (0.073 mol) of sodium heptadecafluorododecyl 2-hydroxy-3-chloropropyl phosphate was charged into a reactor, to which 1000 ml of ethanol was added, followed by agitation and heating to 70° C. to obtain a uniform mixture. Thereafter, the reaction system was cooled down to 30° C., to which was gradually added 40.5 g (0.073 mol) of a 0.0018 mol/g sodium hydroxide ethanol solution, followed by agitation for 4 hours while keeping the temperature. The HPLC analysis revealed the disappearance of a peak of the starting material with a peak for the resultant new product appearing. The resultant NaCl precipitate was removed by filtration and the ethanol was distilled off under reduced pressure to obtain 47 g (yield: 99%) of sodium heptadecafluorododecyl glycidyl phosphate.

|  | Elementary analysis | | | |
|---|---|---|---|---|
|  | C (%) | H (%) | F (%) | P (%) |
| Found | 25.80 | 1.90 | 45 | 4.4 |
| Calculated | 26.24 | 1.91 | 47 | 4.5 |

EXAMPLE 7

50 g (0.11 mol) of sodium octadecenyl 2-hydroxy-3-chloropropyl phosphate was charged into a reactor, to which 1000 ml of ethanol was added, followed by agitation and heating to 70° C. to obtain a uniform mixture. Thereafter, the reaction system was cooled down to 30° C., to which was gradually added 60.0 g (0.11 mol) of a 0.0018 mol/g sodium hydroxide ethanol solution, followed by agitation for 4 hours while keeping the temperature. The HPLC analysis revealed the disappearance of a peak of the starting material with a peak for the resultant new product appearing. The resultant NaCl precipitate was removed by filtration and the ethanol was distilled off under reduced pressure to obtain 46 g (yield: 100%) of sodium octadecenyl glycidyl phosphate.

|  | Elementary analysis | | |
|---|---|---|---|
|  | C (%) | H (%) | P (%) |
| Found | 58.04 | 9.30 | 7.2 |
| Calculated | 59.14 | 9.45 | 7.3 |

EXAMPLE 8

20 g (0.030 mol) of sodium heptadecafluorodecyl 2-hydroxy-3-chloropropyl phosphate was charged into a reactor, to which 500 ml of ethanol was added, followed by agitation and heating to 70° C. to obtain a uniform mixture. Thereafter, the reaction system was cooled down to 30° C., to which was gradually added 16.9 g (0.030 mol) of a 0.0018 mol/g sodium hydroxide ethanol solution, followed by agitation for 4 hours while keeping the temperature. The HPLC analysis revealed the disappearance of a peak of the starting material with a peak for the resultant new product appearing. The resultant NaCl precipitate was removed by filtration and the ethanol was distilled off under reduced pressure to obtain 18.7 g (yield: 99%) of sodium heptadecafluorodecyl glycidyl phosphate.

|  | Elementary analysis | | | |
|---|---|---|---|---|
|  | C (%) | H (%) | F (%) | P (%) |
| Found | 24.96 | 1.40 | 51 | 5.0 |
| Calculated | 25.10 | 1.46 | 52 | 5.0 |

What is claimed is:

1. A phosphoric ester of the formula:

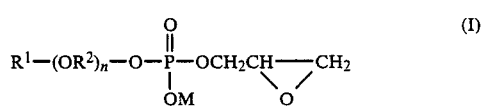

wherein $R^1$ represents a linear or branched alkyl or alkenyl group of 1-36 carbon atoms, a linear or branched fluoroalkyl group of 1-36 carbon atoms, or a phenyl group substituted by a linear or branched alkyl group of 1 to 15 carbon atoms; $R^2$ is an alkylene group of 2 to 3 carbon atoms; n is a value of from 0 to 30; and M represents a hydrogen atom, an alkali metal ion, an alkaline earth metal ion, ammonium, an alkylamine ion or an alkanolamine ion.

2. The phosphoric ester of claim 1, wherein said substituent $R^1$ is a member selected from the group consisting of methyl, ethyl, butyl, octyl, decyl, dodecyl, tetradecyl, hexadecyl, octadecyl, docosyl, tetracosyl, triacontyl, 2-ethylhexyl, 2-octyldodecyl, 2-dodecylhexadecyl, 2-tetradecyloctadecyl, monomethyl-branched isosteryl, tridecafluorooctyl, heptadecafluorododecyl, heneicosafluorododecyl, pentacosafluorotetradecyl, nonacosafluorohexadecyl, tritriacontafluorooctadecyl, 2-pentafluoroethylpentanfluorohexyl, 2-tridecafluorohexyltridecafluorodecyl, 2-heptadecafluorooctylheptadecafluorododecyl, 2-heneicosafluorodecylheneicosafluorotetradecyl, 2-pentacosafluorododecylpentacosafluorohexadecyl, 2-nonacosafluorotetradecylnonacosafluoroooctadecyl, octenyl, decenyl, dodecenyl, tetradecenyl, hexadecenyl, octadecenyl, dococenyl, tetracocenyl, triacontenyl, and nonylphenyl.

* * * * *